US00PP17811P3

(12) United States Plant Patent
Warren et al.

(10) Patent No.: US PP17,811 P3
(45) Date of Patent: Jun. 12, 2007

(54) CALLA LILY PLANT NAMED 'PICANTE'

(50) Latin Name: ***Zantedeschia* spp.**
Varietal Denomination: Picante

(75) Inventors: Andrew G. F. Warren, Tauranga (NZ); Jacobus P. Spaans, Tauranga (NZ)

(73) Assignee: Bloomz Ltd, Tauranga (NZ)

( * ) Notice: Subject to any disclaimer, the term of this patent is extended or adjusted under 35 U.S.C. 154(b) by 63 days.

(21) Appl. No.: 11/183,732

(22) Filed: Jul. 13, 2005

(65) Prior Publication Data

US 2007/0016992 P1 Jan. 18, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Jondle & Associates P.C.

(57) ABSTRACT

A calla lily plant particularly distinguished by orange flowers and sagittate leaves is described.

3 Drawing Sheets

Genus and species: *Zantedeschia* spp.
Variety denomination: 'Picante'.

BACKGROUND OF THE NEW PLANT

The present invention comprises a new and distinct cultivar of calla lily, botanically known as *Zantedeschia* spp., and hereinafter referred to by the cultivar name 'Picante'. The new cultivar was asexually reproduced from vegetative cuttings and tissue culture resulting from the cross of the female parent 'Pot of Gold' (unpatented) and the male parent, 'Neroli' (unpatented).

'Picante' is a product of a planned breeding program intended to create new calla lily plants with orange spathes.

The new cultivar was created in Tauranga, New Zealand and has been asexually reproduced repeatedly by tissue culture in New Zealand. The present invention has been found to retain its distinctive characteristics through successive propagations.

DESCRIPTION OF PHOTOGRAPHS

This new calla lily plant is illustrated by the accompanying photographs which show the mature inflorescence and foliage of the plant. The colors shown are as true as can be reasonably obtained by conventional photographic procedures.

DESCRIPTION OF THE NEW CULTIVAR

Figure 1:
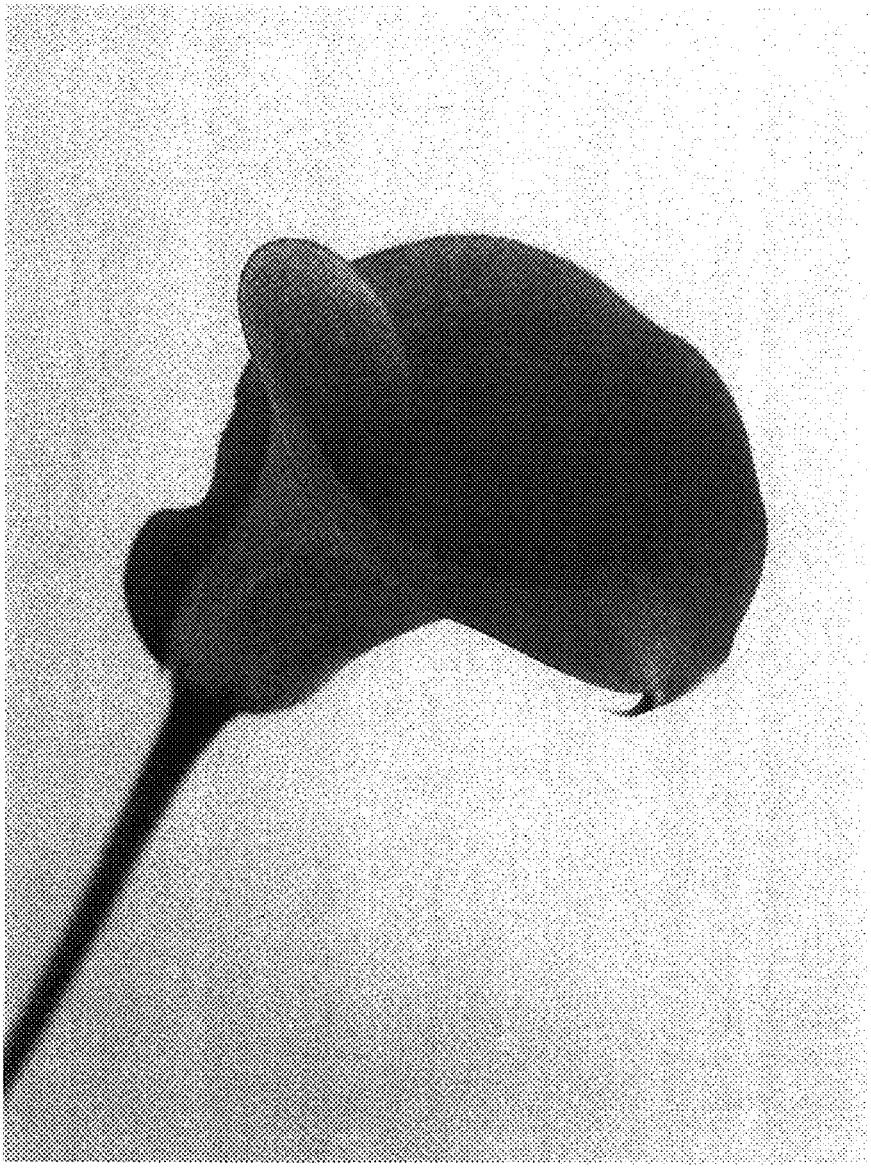
FIG. 1 shows the mature inflorescence.
Figure 2:
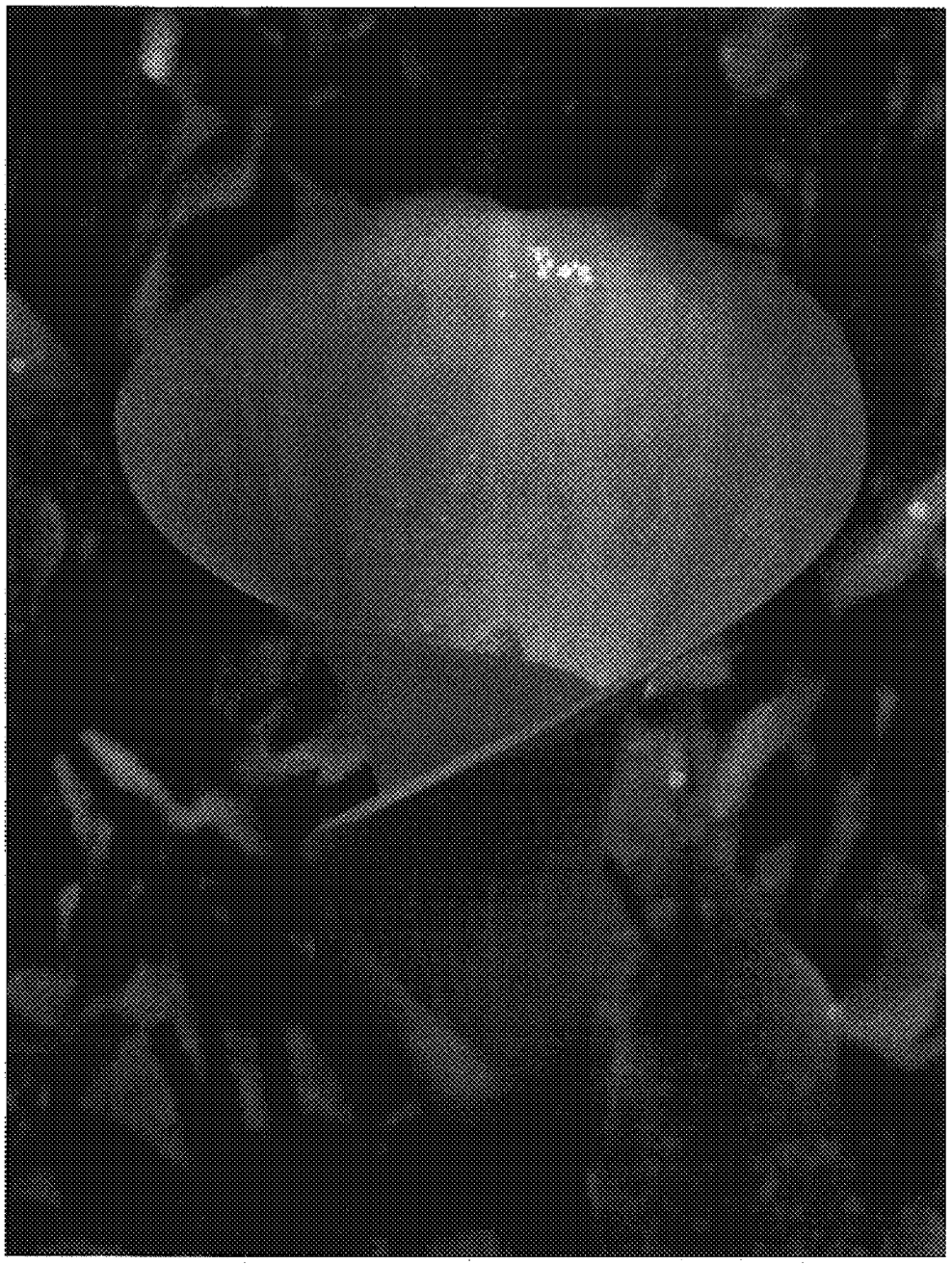
FIG. 2 shows a close-up of the mature inflorescence.
Figure 3:
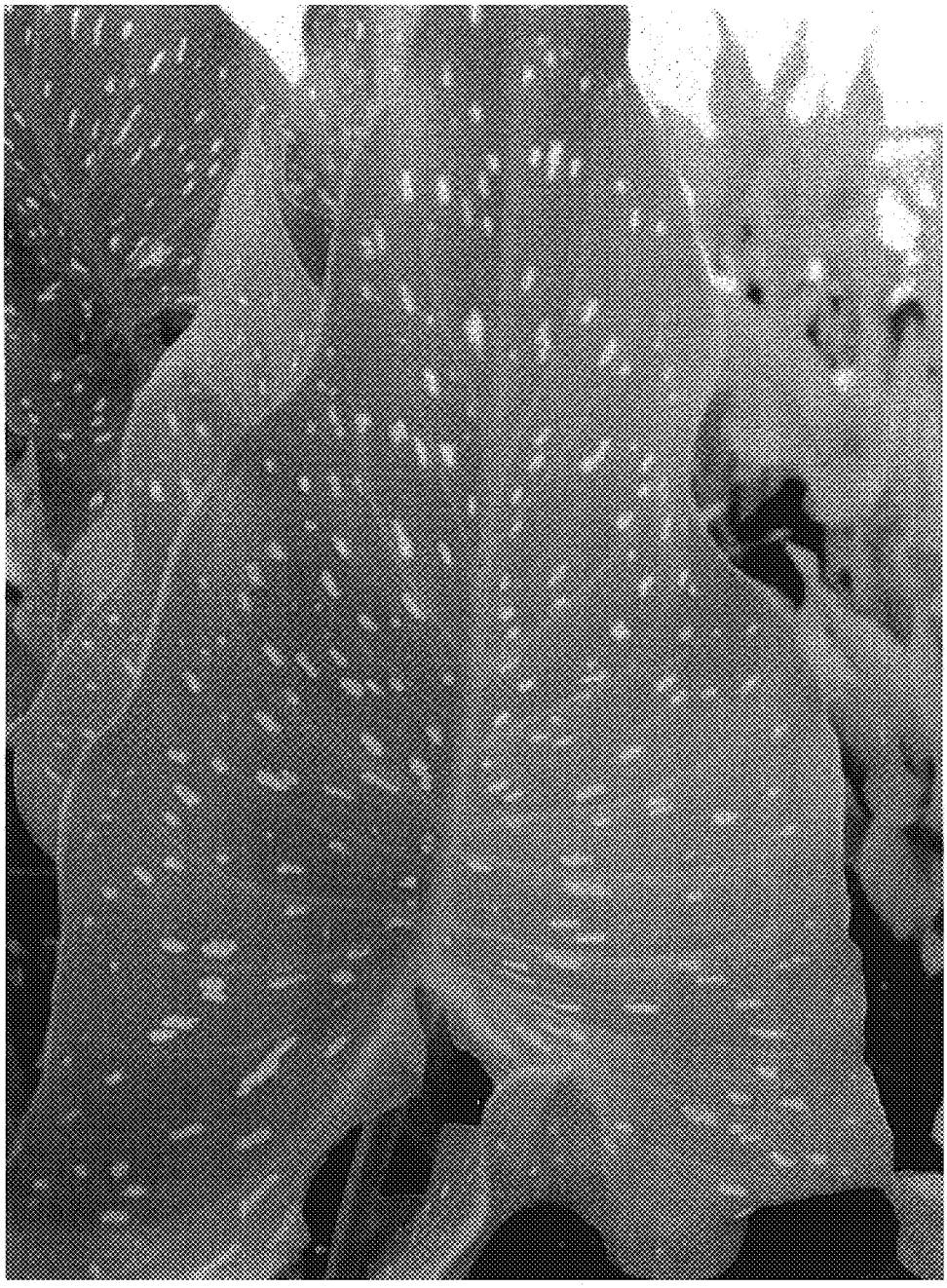
FIG. 3 shows a close-up of the leaf.

The following detailed description sets forth the distinctive characteristics of 'Picante'. The data that define these characteristics were collected from asexual reproductions carried out in New Zealand. The plant history was taken on two-year-old plants based on a 3-cm diameter tuber under New Zealand summer conditions. Color references are primarily to The R.H.S. Colour Chart of The Royal Horticultural Society of London (R.H.S.).

DETAILED BOTANICAL DESCRIPTION

Classification:
- *Botanical name.*—*Zantedeschia* spp.
- *Common name.*—Calla lily.

Size:
- *Form.*—Erect.
- *Height of the leaf canopy above the soil.*—45–60 cm.
- *Height of top of inflorescence above the soil.*—50–65 cm.
- *Diameter.*—25–40 cm.
- *Number of inflorescences per tuber size.*—Tuber diameter 3 cm: 2–4. Tuber diameter 4 cm: 3–5. Tuber diameter 5 cm: 5+.

Leaves:
- *Size.*—Width: 10–14 cm. Length: 20–25 cm.
- *Shape.*—Sagittate.
- *Color.*—Upper surface: RHS 137B. Lower surface: RHS 137C.
- *Maculation* (*leaf spots*).—General: Maculation is only on the upper surface of the leaf but is visible from the lower surface. Density: High density. Color: RHS 155C.
- *Apex.*—Acute to apiculate.
- *Margin.*—Moderately wavy.
- *Margin color.*—RHS 144B (yellow-green).
- *Veins.*—Pinnate.
- *Surface texture.*—Leathery.

Petiole:
- *Average number.*—1 to 3.
- *Length.*—20–25 cm.
- *Diameter.*—0.6–0.8 cm.
- *Color.*—Lower portion: RHS 137D. Upper portion: RHS 137C. Base: RHS 155D.
- *Texture.*—Smooth.
- *Character.*—Strong.

*Sheath.*—Width: 0.7 cm to 0.9 cm. Length: 0.6 cm to 0.8 cm. Color: RHS 36A (pink) and the margin is RHS 46A (red).

Roots:

*Color.*—RHS 155D (white).

*Branching.*—Not branched, attached to the top of the tuber at apices.

Inflorescence:

*Time to produce a finished flowering plant.*—6–10 weeks depending on climate/environment.

*Lastingness of flowers.*—2–3 weeks.

*Fragrance.*—None.

Flower description:

*Spathe* (*flower body*).—Size: Height: 8–10 cm. Width: 5.5–6.5 cm. Color: Upper surface: RHS 26A. Lower surface: RHS 26B. Veins: RHS 26A. Shape: Cup-shaped. Texture: Smooth. Apex: Caudate. Base: Attenuate. Margin: Entire.

*Spadix* (*reproductive organs*).—Size: Length: 2.0–2.5 cm. Diameter: 0.4–0.7 cm. Color: Base: RHS 145C. Upper: RHS 39A. Position relative to spathe: Upright. Shape: Elongated. Apex: Rounded.

*Peduncle* (*flower stem*).—Length: 35–55 cm. Diameter: 0.6–0.9 cm. Color: Base: RHS 155A. Upper: RHS 144A. Texture: Smooth. Strength: Strong.

Reproductive organs:

*Location of female organs.*—Basal position of the spadix.

*Location of male organs.*—Upper position of the spadix.

*Perianth* (*the floral envelope, calyx and corolla*).—Conspicuous.

*Stamens.*—Not visible before pollen release.

*Pollen color.*—White.

*Pistil.*—Number: 20–30 per spadix. Color: RHS 17B.

Fruit:

*General.*—Whole fruit is oval and 3.0–3.5 cm wide and 5.0–6.0 cm long; individual berries are 0.6–0.8 cm in circumference.

*Number.*—10–20 berries.

*Color.*—RHS 145B.

Disease and insect resistance:

*Disease resistance.*—No susceptibility to date.

*Pest resistance.*—No susceptibility to date.

COMPARISON WITH KNOWN CULTIVARS

When the instant plant is compared to the female parent 'Pot of Gold' (unpatented), 'Picante' has orange flowers on a yellow-gold base whereas 'Pot of Gold' has solid gold flowers. The flower shape of 'Picante' is round, whereas the flower shape of 'Pot of Gold' is classic. Additionally, the leaf shape of 'Picante' is sagittate, whereas the leaf shape of 'Pot of Gold' is cordate.

When 'Picante' is compared to the male parent 'Neroli' (unpatented), 'Picante' has orange flowers on a yellow-gold base whereas 'Neroli' has apricot-colored flowers. The flower shape of 'Picante' is round, whereas the flower shape of 'Neroli' is fluted. Additionally, the leaf shape of 'Picante' is sagittate, whereas the leaf shape of 'Neroli' is ovate.

'Picante' differs from the commercial cultivar 'Picasso' (U.S. Plant Pat. No. 15,282) in that 'Picante' has an orange spathe on a yellow-gold base, while 'Picasso' has yellow-orange/purple spathes. Additionally, 'Picante' has a shorter petiole length (20 cm to 25 cm) than 'Picasso' (30 cm to 50 cm).

I claim:

1. A new and distinct cultivar of calla lily plant as shown and described herein.

* * * * *